Aug. 21, 1973 L. E. CARRIER Plant Pat. 3,391
CARNATION PLANT
Filed March 9, 1972
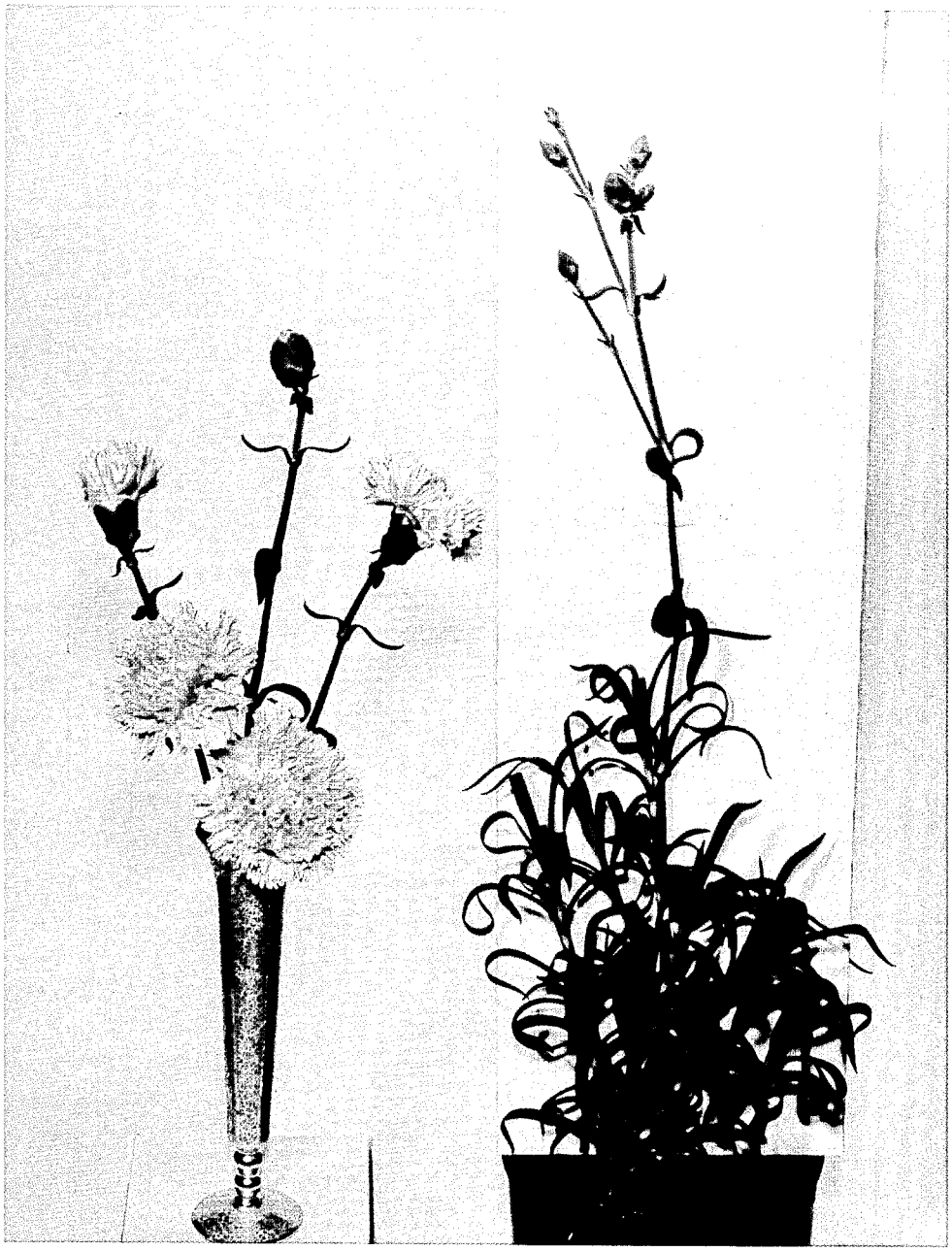

United States Patent Office

Plant Pat. 3,391
Patented Aug. 21, 1973

3,391
CARNATION PLANT

Leonard E. Carrier, 1911 Sheridan Road,
Encinitas, Calif. 92024

Filed Mar. 9, 1972, Ser. No. 233,366
Int. Cl. A01h 5/00
U.S. Cl. Plt.—72 1 Claim The present invention relates to a new and distinct variety of carnation plant which was originated by me by crossing an unnamed and unpatented $F_1$ seedling of the variety known as "Elegance" (unpatented) with an unnamed and unpatented inbred seedling of the variety known as "Sidney Littlefield" (unpatented), the former being the female parent and the latter being the pollen parent.

The primary objectives of this breeding were to produce an improved carnation variety having improved disease resistance and production qualities, along with improved flower color, size and form, as well as less tendency of the calyx to burst and cause "splits" as the flowers open fully, which is so typical of the species botanically known as Dianthus Caryophyllus. These objectives were fully achieved, along with other desirable improvements, as evidenced by the following unique combination of principal characteristics which are outstanding in my new variety, and which distinguish it from its parents, as well as from all other varietes of which I am aware:

(1) A very vigorous and free-breaking plant habit, with strong and straight stems;

(2) Superior resistance to soil-borne diseases such as *Fusarium oxysporium* and *roseum* and other root-rots such as damping off and water molds and the like;

(3) Large, serrated flowers which open fully without bursting the calyx and causing "splits";

(4) A distinctive and attractive pink flower color which fades evenly and beautifully;

(5) A distinctive and pleasing rose-type flower fragrance; and (6) Good heat resistance which is superior to that of the parent lines and the so-called "Sim" varieties.

A sexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

The accompanying drawing shows typical specimens of the vegetative growth and flowers of my new carnation variety in different stages of development and as depicted in color as nearly true as it is reasonably possible to make the same in a color illustration of this character.

The following is a detailed description of my new carnation variety, with color terminology in accordance with Robert Ridgway's Color Standards and Nomenclature (1912 edition), except where general color terms of ordinary dictionary significance are obvious:

Breeding: Seedling.
- Female parent.—An unnamed $F_1$ seedling of "Elegance."
- Male parent.—An unnamed inbred seedling of "Sidney Littlefield."

Classification: Greenhouse type, suitable for cut flower production as a standard (one bloom per stem).

Propagation: Holds its distinguishing characteristics through succeeding propagations by rooted cuttings.

Locality where grown and observed: Encinitas, Calif.

Temperature tolerance: Not hardy to cold, but grows best at temperatures above 10° C.; has good resistance to hot weather in summer months of August and September at Encinitas, Calif. without hardening of growth and with only little reduction of flower size and little flower fading; no marked fading of outer flower petals even when bloom is past maturity.

Blooming period: Blooms under both long and short photoperiods.

Bud: Lobes of calyx overlap in tight bud and seldom split.
- *Length.*—About 3 cm.
- *Diameter.*—Form about 2 cm. to 2½ cm.
- *Color.*—Nickel Green, Plate XXXIII–37".
- *When sepals first divide.*—Color—Spinel Pink, Plate XXVI–71.
- *When petals begin to unfurl.*—Color—Spinel Pink, Plate XXVI–71.
- *When half brown.*—Inside of petals—color—Spinel Pink, Plate XXVI–71. Reverse of petals—color—Thulite Pink, Plate XXVI–71.

Peduncle:
- *Strength.*— Strong.
- *Color.*—Nickel Green, Plate XXXIII–37".

Bloom:
- *Size.*—Diameter—from about 9 cm. to 10 cm. Depth—about 5 cm.
- *Stem.*—Consists of 9 nodes. Length—from about 40 cm. to 60 cm. Diameter—from about 5 mm. to 7 mm. at base, and about 3 mm. at base of calyx. Color—Green.
- *Form.*—Flat-topped when opening, but assumes oval shape when petals reflex and center fully expands.
- *Petalage.*—From 60 to 75 petals. Outer petals—about 5 cm. wide and about 7 cm. long. Center petals—about 3½ cm. wide and about 5 cm. long.
- *Stigmas.*—About 2½ cm. long; curled and do not protrude above petals.
- *Color.*—Center of flower—Spinel Pink, Plate XXVI–71. Outer petals—Deep Rose Pink, Plate XXII–71. Base of petals—Greenish white stalk. Inside of petals—Deep Rose Pink, Plate XXII–71. Reverse of petals—Thulite Pink, Plate XXVI–71. General tonality—Soft even pink tone decreasing in intensity from the center toward outer edge of bloom.
- *Petals.*—Texture—Soft. Form—each petal has 4 or 5 serrations per cm.; outer portions are semi-circular, and inner portions taper in 2 cm. to a 5 mm. stalk; when reflexed, only the stalk is inside the calyx.
- *Opening.*—Outer petals expand before the center petals, allowing the petals to expand beyond the calyx before the center petals reach full size, so that petals and flowers attain an exceptionally large size without bursting the calyx and causing "splits"; the calyx itself differs from the usual "Sim" varieties in being relatively short, with the lobes overlapping in the bud and allowing the large development without bursting.
- *Fragrance.*—A distinctive and pleasing rose type fragrance.

Plant:
- *Form.*—Erect, but free-branching.
- *Growth.*—Very vigorous and rapid; cuttings produce shoots from all nodes except the upper 6 which have flower buds; averages 9 or 10 shoots per cutting, as compared with 4 to 6 shoots normally produced by the "Sim" varieties.

Foliage:
- *Form.*—From flat to nearly concave.
- *Size.*—About 8 mm. wide and from about 12 cm. to 14 cm. long.
- *Quantity.*—Two leaves per node, with nodes spaced about 7 cm. to 8 cm. apart.
- *Color.*—Young—upper side—Leaf Green, Plate XLI–29"; under side—same. Mature—upper side—

Nickel Green, Plate XXXIII–37"; under side—same.

*Texture.*—Smooth.

Disease resistance: The new variety has shown no evidence of Fusariums or other root rots, as determined by extensive tests in highly infested soils innoculated with as many strains of fungi as are locally available in the area of Encinitas, Calif.; tests conducted without chemical or steam sterilization of the soil.

I claim:

1. A new and distinct variety of carnation plant, substantially as herein shown and described, characterized particularly as to novelty by the unique combination of a very vigorous and free-breaking plant habit, with strong and straight stems, superior resistance to soil-borne diseases such as *Fusarium oxysporium* and *roseum* and other root-rots such as damping off and water molds and the like, large, serrated flowers which open fully without bursting the calyx and causing "splits," a distinctive and attractive pink flower color which fades evenly and beautifully, a distinctive and pleasing rose-type flower fragrance, and good heat tolerance which is superior to that of the parent lines and the so-called "Sim" varieties.

No references cited.

ROBERT E. BAGWILL, Primary Examiner